(12) United States Patent
Sambusseti (10) Patent No.: US 10,617,513 B2
(45) Date of Patent: Apr. 14, 2020

(54) PGA TUBULAR PATCH AND RELATIVE OPTIONAL TUBULAR SUPPORT MADE OF ABSORBABLE MATERIAL FOR THE TISSUE RECONSTRUCTION OF URETHRAL AND/OR URETERAL REMOVED SEGMENTS

(71) Applicant: Antonio Sambusseti, Cremona (IT)

(72) Inventor: Antonio Sambusseti, Cremona (IT)

( * ) Notice: Subject to any disclaimer, the term of this patent is extended or adjusted under 35 U.S.C. 154(b) by 0 days.

(21) Appl. No.: 15/028,975

(22) PCT Filed: Oct. 14, 2014

(86) PCT No.: PCT/EP2014/072064
§ 371 (c)(1),
(2) Date: Apr. 13, 2016

(87) PCT Pub. No.: WO2015/055684
PCT Pub. Date: Apr. 23, 2015

(65) Prior Publication Data
US 2016/0262865 A1    Sep. 15, 2016

(30) Foreign Application Priority Data

Oct. 16, 2013    (IT) .............................. MI2013A1716

(51) Int. Cl.
*A61F 2/04* (2013.01)
*A61L 27/36* (2006.01)
(Continued)

(52) U.S. Cl.
CPC ............ *A61F 2/04* (2013.01); *A61L 27/3679* (2013.01); *A61L 27/3878* (2013.01);
(Continued)

(58) Field of Classification Search
CPC ............. A61L 27/3679; A61L 27/3878; A61L 2430/22; A61F 2/04; A61F 2002/047; A61F 2002/048
See application file for complete search history.

(56) References Cited

U.S. PATENT DOCUMENTS

| 6,537,567 B1 * | 3/2003 | Niklason | ............... | A61L 27/507 |
| | | | | 424/422 |
| 2002/0055786 A1 | 5/2002 | Atala | | |

(Continued)

FOREIGN PATENT DOCUMENTS

| IT | MI20 120 646 A1 | 10/2013 |
| WO | 2005/089673 A1 | 9/2005 |

(Continued)

OTHER PUBLICATIONS

R.C. Thomson, M.C. Wake, M.J. Yaszemski, A.G. Mikos; Biodegradable Polymer Scaffolds to Regenerate Organs; 1995; Springer-Verlag Berlin Heidelberg; Advances in Polymer Science vol. 122; 247-266.*

(Continued)

*Primary Examiner* — William H Matthews
(74) *Attorney, Agent, or Firm* — Young & Thompson (57) ABSTRACT

A tubular patch (3) made of PGA fabric, optionally containing within it a mesh tubular support in PGA/PLA, for implantation to replace one or more urethral and/or ureteral removed segments for use in tissue reconstruction of the removed segments for the treatment of diseases such as necrosis, stenosis, tumours, trauma, iatrogenic injuries and the like, or congenital malformations.

19 Claims, 4 Drawing Sheets

(51) Int. Cl.
*A61L 27/38* (2006.01)
*A61L 27/18* (2006.01)
*A61L 27/58* (2006.01)
*A61L 27/56* (2006.01)
*A61L 27/50* (2006.01)

(52) U.S. Cl.
CPC ... *A61F 2002/047* (2013.01); *A61F 2002/048* (2013.01); *A61F 2210/0004* (2013.01); *A61F 2230/0069* (2013.01); *A61L 27/18* (2013.01); *A61L 27/50* (2013.01); *A61L 27/56* (2013.01); *A61L 27/58* (2013.01); *A61L 2430/22* (2013.01)

(56) References Cited

U.S. PATENT DOCUMENTS

| | | |
|---|---|---|
| 2010/0331864 A1 | 12/2010 | Shetty et al. |
| 2013/0173015 A1 | 7/2013 | Ludlow et al. |
| 2013/0317622 A1 | 11/2013 | Sambusseti et al. |

FOREIGN PATENT DOCUMENTS

| | | |
|---|---|---|
| WO | 2011/004388 A2 | 1/2011 |
| WO | 2011/064110 A1 | 6/2011 |
| WO | 2011/082295 A2 | 7/2011 |
| WO | 20130135544 A1 | 9/2013 |

OTHER PUBLICATIONS

International Search Report, dated May 6, 2015, from corresponding PCT application.

\* cited by examiner

PGA TUBULAR PATCH AND RELATIVE OPTIONAL TUBULAR SUPPORT MADE OF ABSORBABLE MATERIAL FOR THE TISSUE RECONSTRUCTION OF URETHRAL AND/OR URETERAL REMOVED SEGMENTS

The present invention refers to a tubular patch made of PGA fabric for use in tissue replacement and reconstruction of natural urethral and/or ureteral removed segments.

In particular the present invention refers to an absorbable tubular support for supporting any tubular patch to replace natural urethral and/or ureteral removed segments for use in the tissue reconstruction of said removed segments.

More specifically the present invention refers to the implant obtained from the combined use of said support and said tubular patch.

The urethra and/or ureters may require surgical "repair" when affected by certain diseases such as stenosis, tumours, necrosis, trauma, iatrogenic injuries and the like, or congenital malformations.

Said surgical repair consists in the removal of a damaged segment of urethra and/or ureters and replacement thereof with flaps of autologous tissue taken from the patient in order to reconstruct the removed tissue part.

Generally these flaps come from the intestine, the oral mucosa and also the peritoneal tissue.

Although autologous tissue guarantees absence of rejection by the patient, it does not have the same elastic characteristics typical of the ureters and urethra or the impermeability to urine as it does not have urothelial cells.

To overcome said drawbacks it is therefore highly desirable for an implant (or implantable prosthetic device) for the replacement of removed segments of ureter and/or urethra to be elastic, flexible and made of a biocompatible material which behaves very similarly to the natural tissue removed in terms of elasticity and impermeability to urine.

Furthermore it is highly desirable for said device not to bend under the weight of the autologous growing tissue so that the lumen for passage of the urine in the implanted device is not significantly reduced with respect to the natural lumen of the ureter/urethra.

Said reduction of the lumen must in fact be avoided since even the smallest kidney stone, which is normally expelled through the ureter without any problems, could cause the obstruction thereof and could even completely close the passage.

The patent application WO 2005/089673 A1 describes a medical device useful also for replacing segments of ureter, which is formed of an outer porous scaffold, in the pores of which the tissue will regrow, and an inner device, preferably solid without inner lumen, which must be removed after the above-mentioned tissue has grown on the outer scaffold.

The patent application US 2013/0173015 A1 describes a scaffold for the replacement of ureter, urethra and bladder tissues, which is coated with cultured autologous cells and is optionally reinforced with reabsorbable materials.

The patent application WO 2011/004388 describes a tissue graft for urological structures, formed of a tubular scaffold surrounded by a biocompatible and/or bioabsorbable shaped setting material, wherein said outer shaped setting material is coated with in vitro cultured cells.

Said known implants, which are implanted in the patient only after being coated with an autologous or allogeneic cell population cultured in a genetic laboratory, are fairly complex, costly and lengthy to be produced, given that before the cell coating phase a series of long and complex preparatory phases are required, such as isolation of the cells to be cultured by means of biopsy, growth of the number of isolated cells, and population and pre-treatment of the surface of the tubular patch so that it can be populated by the cells.

The object of the present invention is to overcome, at least partly, the drawbacks of the known art, providing an implant for the replacement and reconstruction of one or more removed urethral and/or ureteral segments which has substantially the same elastic characteristics, and which is easy and simple, and also inexpensive, to produce.

A further object is to provide an implant as defined above which furthermore has substantially the same characteristics of impermeability to urine typical of the ureters and urethra and which does not have to be surgically removed after the grafting.

A further object is to provide an implant as defined above which avoids even the slightest reduction in the lumen of the regrowing tissue segment to ensure that the dimensions of the natural lumen are maintained.

These and other objects are achieved by the tubular implant, optionally comprising an inner support, according to the invention and having the characteristics listed in the attached independent claim 1.

Advantageous embodiments of the invention appear in the dependent claims.

A first subject of the present invention concerns a prosthetic medical device for implanting in a human or animal body, in the form of a reabsorbable biocompatible tubular patch, suitable for the reconstruction, repair or replacement of one or more urethral and/or ureteral segments removed following their resection for the treatment of diseases such as necrosis, stenosis, tumours, trauma, iatrogenic injuries and the like, or congenital malformations, said patch being made of a PGA fabric without any inner support.

The term "patch" here identifies soft substrates, in the form of a flat sheet or in a tubular form, used in medicine to repair soft tissues, provided with greater flexibility and elasticity than the scaffolds and mesh or mesh tape substrates or reinforcement meshes. The present tubular device for implantation can therefore either be obtained from a flat fabric which is then shaped in situ during surgery, or can be a single piece in tubular form ready for surgical use.

The Applicant has found that the PGA patch according to the invention can be implanted in the patient or in the animal without having to be coated, completely or partially, with cultured tissue cells (culture cell seeding) previously grown in vitro and/or without having to be surface-treated to promote engraftment during regrowth of the autologous tissues.

This represents one of the main advantages of the tubular device as defined above.

In practice, the above-mentioned patch has proved suitable for acting as a scaffold after insertion in the patient, causing growth on it only of autologous cells from a fibrotic capsule, generated by the tissue reconstruction process of the patient which takes place only after the implantation of said patch in the patient.

Said tubular patch made of PGA fabric and without inner support has also proved able to support the autologous tissue during regrowth on it, thus substantially maintaining a constant lumen in the section of ureter and/or urethra during regrowth.

Furthermore the above-mentioned PGA fabric was found to be neutral when in contact with the new tissue during regrowth: this entails a rapid population of the device implanted by the cells of the surrounding tissue during growth. At the same time the adhesion was reduced due to the negligible interaction between the PGA fabric and the biological molecules, thus guaranteeing non-fusion with the inner tissues of the patient.

PGA is a biodegradable thermoplastic polymer characterised by a high degree of crystallinity, around 45-55% in the case of the homopolymer. Although said material is degraded by random hydrolysis processes, and also by some classes of enzymes, in particular belonging to the esterase family, it does not deteriorate in contact with urine for a period of at least two months, not showing any swelling (increase in volume and dimensions) during said period.

PGA also has a degradation time ranging from 4 to 6 or even 12 months, but begins to lose its mechanical resistance after 4 weeks and it is completely lost by the fifth month. This is compatible with the cell growth of the urethra/ureter tissues.

Said PGA fabric is produced using a multifilament or ultralight monofilament yarn, deriving from fibres of PGA (polyglycolide or polyglycolic acid).

The preferred PGA fibres for production of the above-mentioned fabric are those deriving from the homopolymer which are very rigid and characterised by a high tensile modulus value of 7 GPa and a tensile strength of at least 4.5 grams/denier.

Due to these properties, the fabric obtained using said PGA fibres has a sufficient mechanical strength while allowing the fabric to be flexible.

The PGA fabric of the patch of the present invention can be produced by braiding said PGA monofilament or multifilament in various ways, creating a knit fabric, a woven fabric or a non-woven fabric.

It is preferable to use a knit fabric, in particular warp knit, as it has a rougher surface than the other types mentioned above.

Furthermore said fabric is preferably a warp knitted fabric: the warp knitting process does not result in a woven or a non-woven fabric, and neither in a felt-like material.

The warp knitting process is carried out on a warp knitting machine where the yarns are woven parallel and knitted at the same time with a density of preferably 30 needles/inch.

In this case the fabric weft is such that the interstitial space is less than 200 microns, preferably around 160 microns, corresponding to a mean hole area of approximately 0.02 mm$^2$. This guarantees impermeability to urine, avoiding leaks.

Preferably the weaving pattern of said warp knitting process is of the following type:

| | |
|---|---|
| Wales Per Inch (WPI) | 29-30 |
| Courses Per Inch (CPI) | 62-68 |

With this weaving pattern and with the preferred yarn as above, a fabric is obtained having the following specifications:

| | |
|---|---|
| Mean area (mm$^2$) | 0.020 |
| Effective diameter (microns) | 140-180 |
| Porosity | 70-80% |
| Surface density, mg/cm$^2$ | 16-18 |

Furthermore it is also preferable for the PGA patch fabric to be textured. In fact, it has been found that texturing, in addition to giving the fabric a rougher surface, also provides greater impermeability to urine than a non-textured fabric. It is assumed that texturing provides greater coverage of the micro-holes between the fabric stitches.

Texturing of the fabric can be achieved in various ways: by the use of monofilament with rough surface obtained according to the methods known in the art, or by means of heatsetting of the fabric to obtain reliefs in the fibres giving the filament greater volume. The latter texturing method is preferred.

Said PGA fabric can also be reinforced by applying to the flat fabric one or more strips of said PGA fabric and then obtaining the tubular device from the reinforced flat fabric.

A further subject of the present invention concerns a tubular support with three-dimensional structure, flexible, to support a tubular patch made of a reabsorbable or non-reabsorbable polymeric material, preferably made of PGA (polyglycolic acid) fabric, more preferably PGA warp knit fabric, for use in the replacement of one or more natural urethral and/or ureteral removed segments, said support being a mesh structure or provided with openings, and produced by means of moulding and/or thermoforming of a PLA/PGA polymer, preferably PLLA/PGA, in particular PLLA/PGA.

Said tubular support, while being flexible and provided with openings or meshes, generally very narrow, is not radially expandable with a radial rigidity such as to support the tubular patch and the autologous tissue during growth on said patch, acting in practice as a scaffold, also during reabsorption thereof. This is due to the combination of the specific material with the structure and the process via which it is obtained, which gives the mesh support a greater rigidity than the tubular patches for use in the reconstruction of urethra and/or ureter segments on which the new autologous tissue regrows.

Since said support is able to withstand the radial stress of the new tissue growing on the tubular patch, it avoids both substantial and minimum reductions in the lumen of the tubular tissue segment during regrowth.

The present support is highly bioabsorbable since its degradation time is closely coordinated with the formation time of the new autologous tissue of the ureter or urethra.

Said support does not entail any pre-treatment prior to the implant, such as swelling, for example.

Since said support is not inserted completely inside the ureter, it also acts as a connecting element between the two free ends of the ureter segments remaining after removal of the necrotic part.

In practice, the combined use of the present support with the tubular patch or device results in an improved implant for the replacement of one or more ureteral and/or urethral removed segments since it cannot be deformed after implantation, thus overcoming the drawbacks of the known art.

Said implant can be constructed during surgery using a flat patch to be wrapped externally around the support, or can be prepared separately as a single piece ready for implantation "as is" during surgery, as will be explained below: in both cases, however, the support is, in use, in contact with the inner surface of said patch without any free space between the two elements.

In the case of an implant ready for use, the tubular patch will necessarily be shorter than the support to facilitate fixing of the edges of the support to the free ends of the ureter. The polymer of the support, indicated above as PGA/PLA (poly(lactic-co-glycolic acid)), is a copolymer of lactic acid and glycolic acid where the abbreviation PLA here identify the poly(lactic) acid deriving from any type of molecule of lactic acid (chiral molecule): in fact there are different types of polymer indicated by specific abbreviations such as PDLA, PLLA, PDLLA, where D and L represent the two stereoisomers of the lactic acid, the L-lactic acid and the D-lactic acid. The PLLA (poly(L-lactic) acid) has a crystallinity of 37%, a glass-transition temperature of between 50 and 80° C., and a melting temperature of 173-178° C., whereas the polymer deriving from the polymerization of a racemic mixture of D and L isomers, the PDLLA, is amorphous.

It is also possible to use a polymeric mixture (blend) of the two single PLA polymers as defined above and PGA.

Preferably PLLA is used as the PLA.

Generally the copolymer PLLA/PGA (or mixture of PGA and PLLA) is formed of 30% PGA and 70% PLLA; preferably as PLLA/PGA, a poly(L-lactic-co-glycolic) copolymer (PLLA/PGA) is used in which the L-lactic acid is 82-88% in moles while the glycolic acid is 18-12% in moles.

Said specific material makes it possible to obtain a support with the necessary mechanical rigidity to hold the tubular patch on which the autologous tissue of the ureter/urethra regrows, but without reducing the elasticity thereof.

Said balance between rigidity and elastic properties cannot be obtained if only PGA or PLA is used.

Said support is preferably obtained by moulding, for example injection or compression moulding, and/or thermo-forming of the PGA/PLA. Alternatively, it is also possible to obtain a very fine tubular support by means of extrusion and subsequent cutting of the mesh using plastic cutting technologies to directly obtain the desired geometry, without the need for mechanical or thermal joints.

The diameter of the support for the tubular device depends on what segment has to be replaced:

in the case of the urethra, said support has a diameter of 10 mm (adults) and 6 mm (paediatric) while the length is 7 mm;

in the case of ureters, said support has a diameter of 5 mm (adults) with length from 3 cm to 30 cm, generally 15 cm, whereas for paediatric use the support has a diameter of 3 mm with a length from 3 cm to 10 cm.

The thickness of the support generally ranges from 0.056 mm to 1.15 mm or is in any case extremely fine in order to offer minimum resistance to the urinary flow.

The support described previously supports a tubular patch made of an appropriate material which acts, in turn, as a bioactive material since it promotes the growth of the biological tissue on the surface of said patch.

If the present implant including inner support is obtained during surgery, the flat patch is wrapped externally around the support connecting the two free ends of the ureter and is sewn longitudinally with suture thread (reabsorbable or non-reabsorbable according to the type of patch material) to form a tubular structure or tube around the support.

The polymer used to produce the patch including inner support is a biocompatible material, and can be of reabsorbable or non-reabsorbable type, preferably a PGA fabric, more preferably in PGA warp knit fabric, so as not to cause any type of alteration in the tissues with which it comes into contact.

Other biocompatible polymers used to produce the patch (in flat or tubular form) of the present supported tubular device, other than PGA, are for example polylactic acid (PLA), polycaprolactone (PCL) or mixtures thereof.

Further polymers that can be used as patches and are normally used in the medical field can be silicone, polysulphone, PE, PP, Dacron (PET), PTFE, PVC, polypropylene and polystyrene, Nylon (66 or 6), Kevlar and more generally synthetic Polyamides, Mylar, PE, Polyurethanes (Biomer, Pellethane, Corethane and Tecooflex) and Polyureas, Poly-acrylates and others, preferably integrally coated by a layer of pyrolytic turbostratic carbon having thickness generally around 0.2-0.3 micron, to improve the bio compatibility.

Although the strength of the above-mentioned materials is such as to ensure the absence of substantial variations in the dimensions of the natural lumen, the use of a patch support in said materials is nevertheless advantageous as it ensures that the lumen is not subject to any, even minimum, reduction in dimension.

An example of said materials alternative to PGA could be a membrane made of soft, flexible elastic silicone, coated completely in pyrolytic turbostratic carbon with thickness of approximately 0.2-0.3 micron on both sides of the membrane.

Said layer of pyrolytic turbostratic carbon is applied according to the known technique for obtaining ultrafine films in the order of a few microns, for example using a PVD (Physical Vapour Deposition) method.

Said pyrolytic turbostratic carbon coating is neutral when in contact with the cells of the new urethral and/or ureteral tissue during growth: this entails rapid population of the present patch by the cells of the new tissue and an accelerated assimilation of the same, once implanted.

At the same time the adhesion of the fibrotic capsule is reduced due to the reduced interaction between the coated surface and the biological molecules. This ensures a substantial absence of the phenomenon of fusion with the surrounding tissues which generally occurs when other artificial materials are used in reconstructive surgery, for example a membrane made solely of silicone.

Furthermore the surfaces of the present tubular device coated in pyrolytic turbostratic carbon are smooth, free from encrustation and urine-resistant.

The silicone used for the tubular patch with inner support of the present invention can consist, for example, of copolymers of dimethyl- and methyl vinyl siloxane, reinforced with silicon.

Preferably a medical silicone is used, for example the one known as MED 4735™ and marketed by Nusil Technology. This silicone has properties, such as elongation and tensile strength, which are particularly suitable for application in the construction of a tubular device for the replacement of urethral and/or ureteral segments.

If the patch including inner support is made of non-reabsorbable material, it must obviously be removed after a certain period of time from the graft.

When the flat patch to obtain the non-reabsorbable tubular device with inner support derives from a membrane, it can also incorporate a Dacron reinforcement mesh within its thickness so as to facilitate suturing of the device to the urethra and/or ureters, avoiding the tearing of said sutures, and/or to provide greater rigidity according to requirements.

The inner diameter of said tubular patch or device, with or without inner support, according to the present invention, depends on the type of natural segment that has to be replaced:

in the case of the urethra, said tubular patch or device has an internal diameter that varies from 16 to 24 Ch max (1 Charrier=⅓ mm);

in the case of ureters, said tubular patch or device has an internal diameter that varies from 6 to 10 Ch max.

The thickness of the tubular patch or device, with or without inner support according to the present invention, can vary from 0.1 micron to 80 micron, preferably around 20-30 micron.

Figure 1:
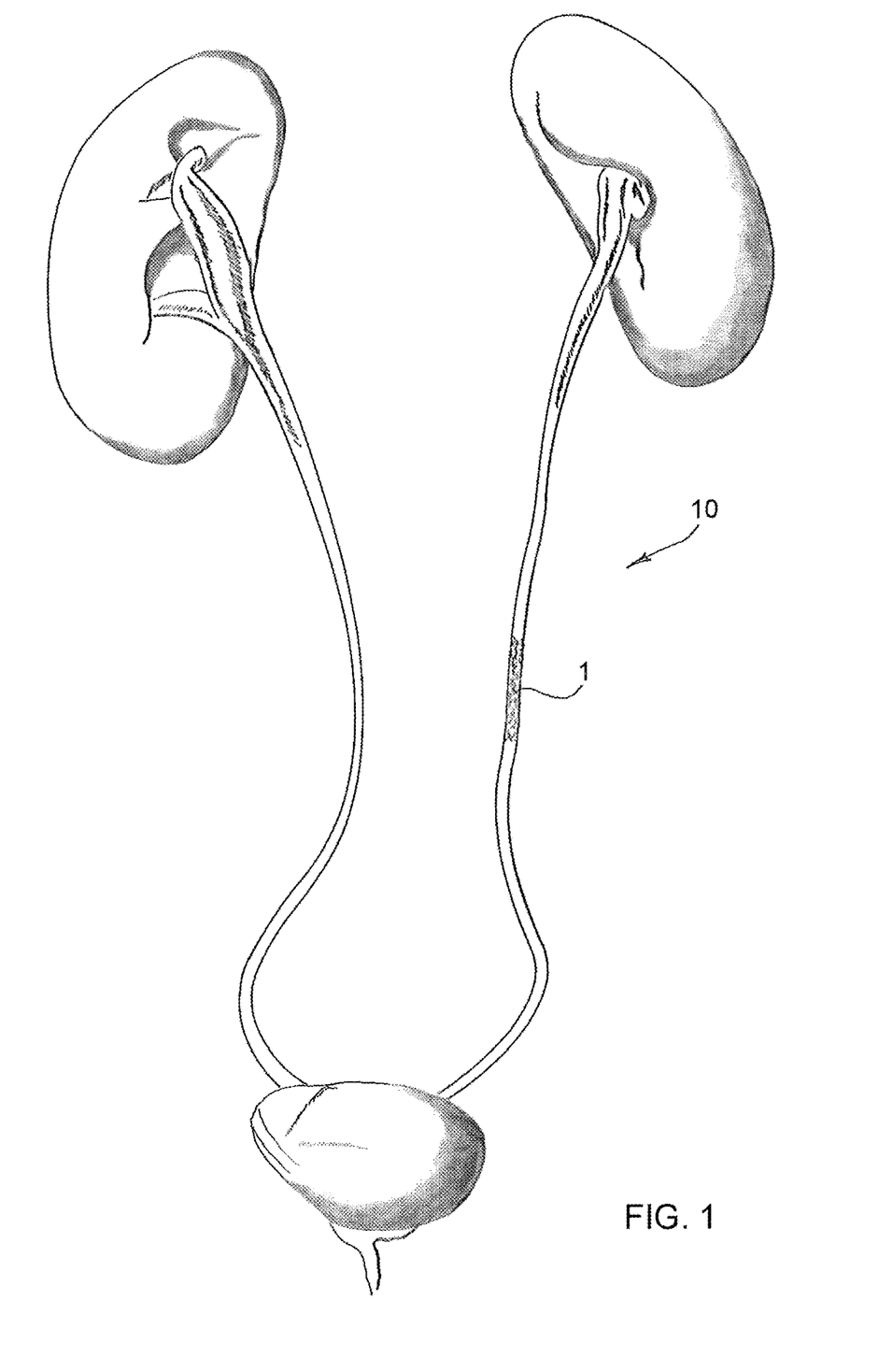
FIG. 1 is an overview of a human urinary system comprising kidneys, ureters, bladder and urethra with one ureter affected by necrosis (dark portion)

Further characteristics of the invention will become clearer from the following detailed description, referring to an embodiment thereof, provided by way of non-limiting example, illustrated in the attached drawings, in which:

FIG. 1 illustrates a ureter affected by necrosis where the necrotic area (segment) to be removed is indicated by the reference number 1.

The following description applies also if the necrotic area 1 is on the urethra instead of on the ureter and if the urethra and/or ureter are affected by diseases other than necrosis, such as stenosis, tumours, trauma, iatrogenic injuries and the like, or congenital malformations.

Figure 2:
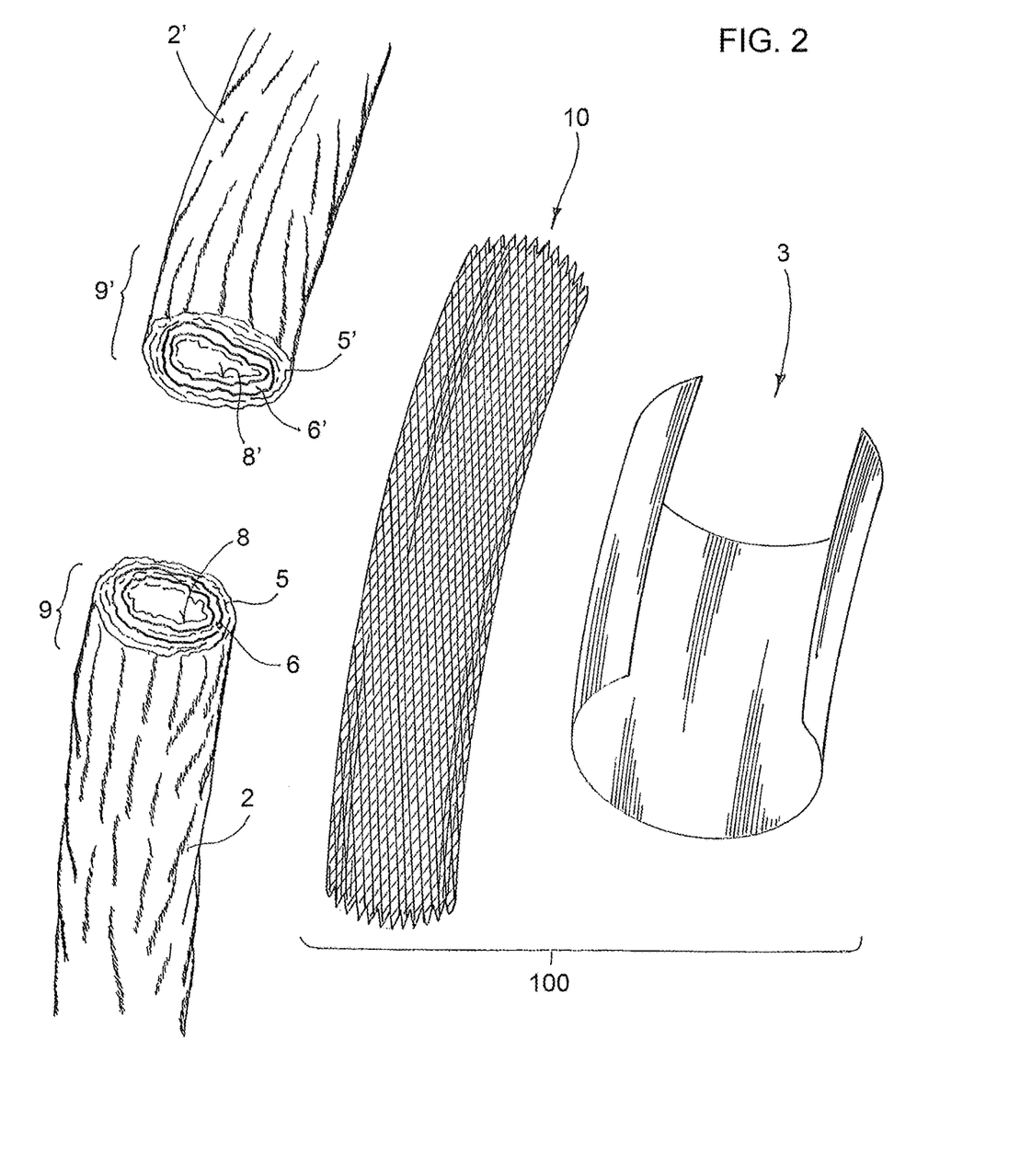
FIG. 2 is a partial perspective view of the ureter of FIG. 1 from which the necrotic segment has been removed and will be replaced during surgery by the implant according to the invention illustrated in exploded view (flat patch and relative support)

The surgical removal of the necrotic area 1 generates two separate ureter segments, indicated in FIG. 2 by the numerical reference 2, 2', which will be re-connected to each other by insertion, in the missing section, of the tubular implant of the present invention consisting of a tubular patch and relative support, to replace the removed area 1.

Without departing from the scope of the present invention, the following description and teachings apply also if the tubular implant of the present invention consists only of a tubular patch made of PGA fabric without inner support.

Figure 3A:
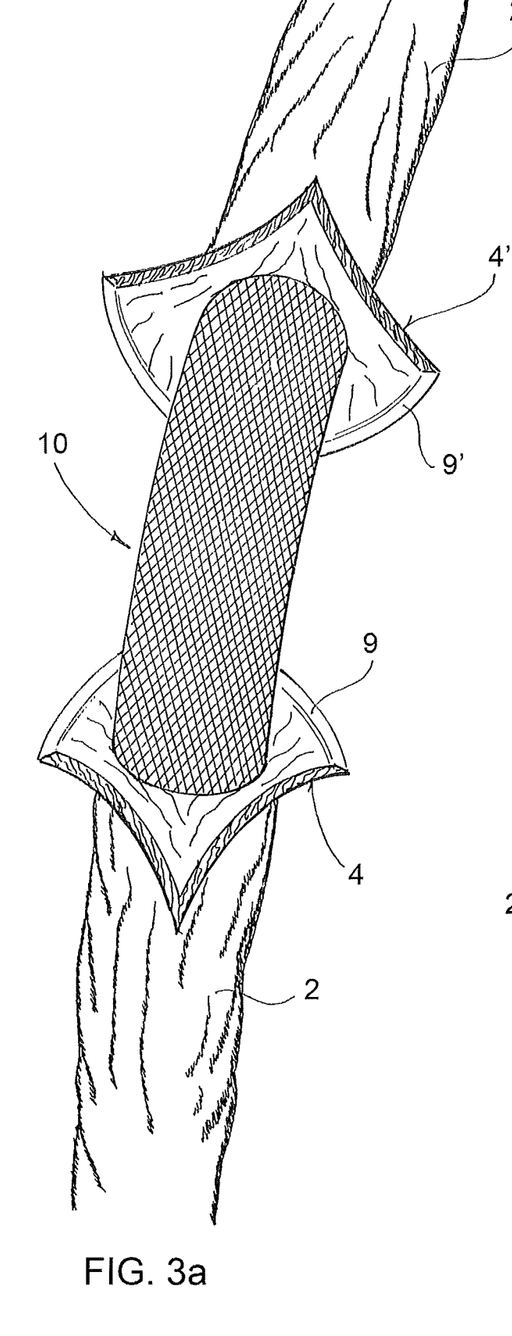
FIGS. 3a) and 3b) illustrate respectively insertion of the support of the tubular device, ready for use, in the section of the ureter removed and subsequent suturing.
Figure 3B:
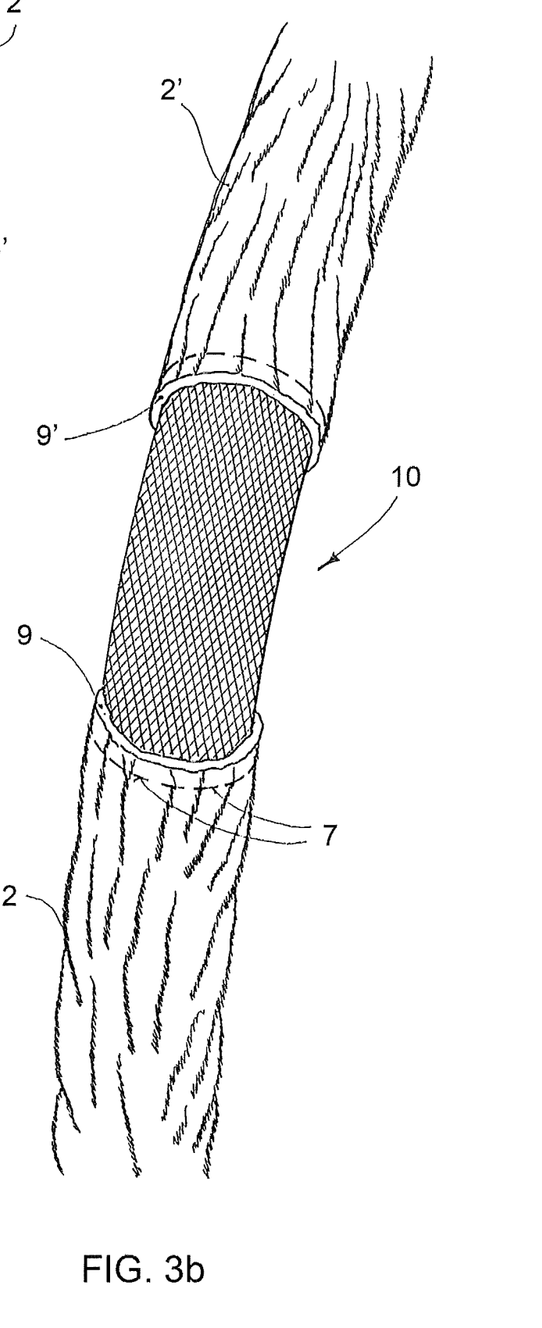

Said implant can be supplied already formed with the external patch in one single tubular piece, or it can be formed by the surgeon during the operation as will now be explained below. FIGS. 3a and 3b show the mesh support 10 inserted into respective lumens 8, 8', in the area of the free ends of the two detached ureter segments 2, 2'.

The first stage is insertion, via the urethra, of a double J catheter or stent (not illustrated in the figure) into the ureter having the necrotic area to free the ureter from any blockages. Once the catheter has been withdrawn from the ureter, resection of the necrotic section 1 can be performed.

After carrying out the resection (removal) of the segment 1 of the damaged ureter, the edges of the mesh support 10 are inserted into respective lumens 8, 8' (FIGS. 3a and 3b), in the area of the free ends of the two detached ureter segments 2, 2'.

To improve understanding of the present invention, FIG. 3a shows in exploded view the edges of the detached segments 2, 2' in the area of their respective free end deriving from an incision 4: said incision 4 is not strictly necessary, even though it facilitates insertion of the ends of the support 10 into the lumen 8, 8' (FIGS. 3a and 3b) in the area of the free ends of the two ureter segments as it will be explained in detail hereinafter. In the case of incision 4, the edges must then be sutured longitudinally with reabsorbable thread, thus restoring the tubular form.

After inserting, generally in a forced manner, the edges of the support 10 into the lumen 8, 8' of the free ends of the ureter segments, said edges of the support 10 are sutured along the circumference of both the free ends of the two ureter segments, as illustrated in FIG. 3b), using sutures 7 made of suture thread with diameter 3/0 or 4/0, in reabsorbable material, for example PGA, MONOTIME® absorbable or similar.

Figure 4:
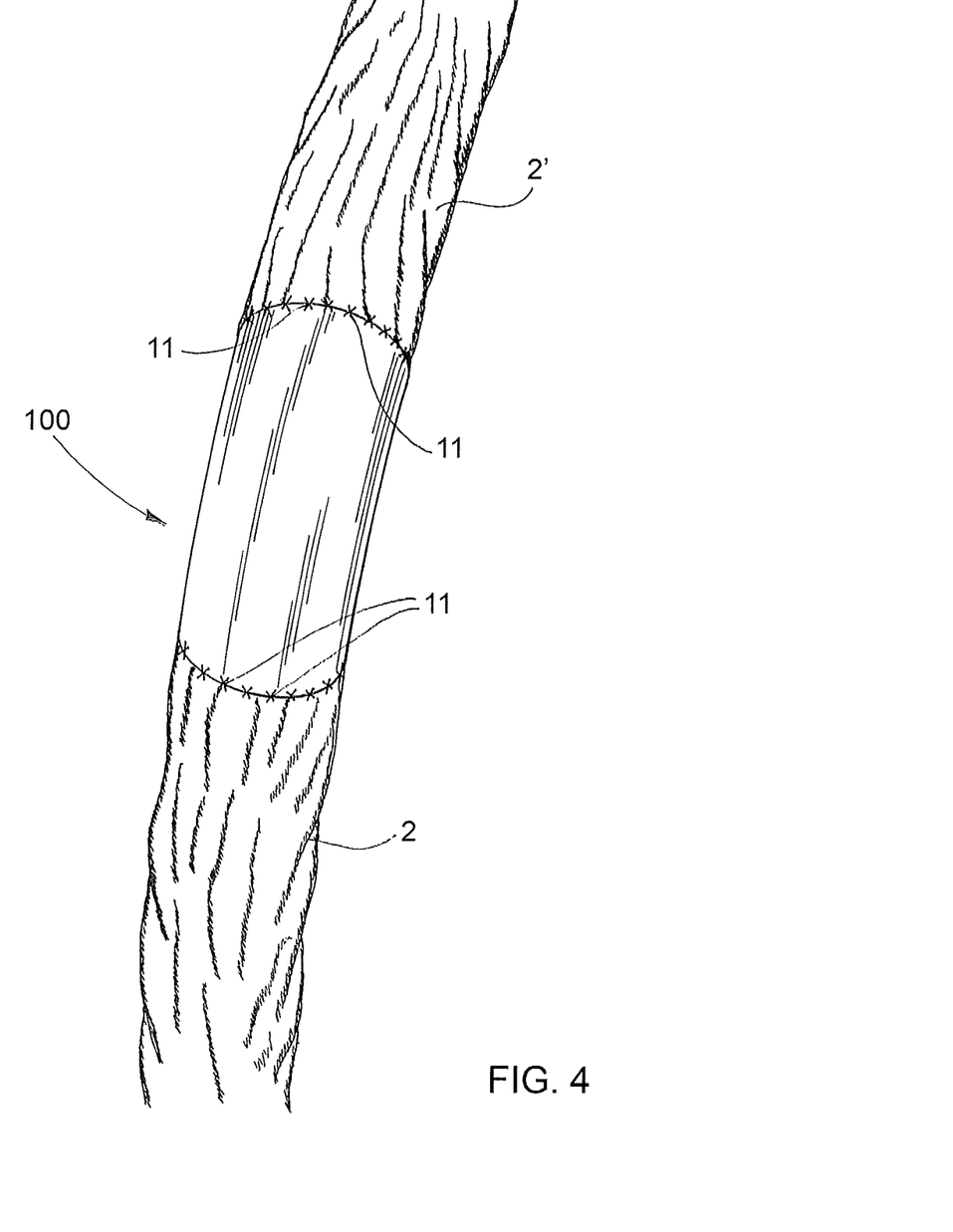
FIG. 4 illustrates the flat patch of FIGS. 3a and 3b wrapped around the support of FIG. 2 to form, during surgery, the tubular device in the section of ureter removed.

Subsequently the rectangular patch 3, in the form of a flat membrane and made of textured PGA fabric, with a length shorter than the support 10, is wrapped around the support 10 so as to be in contact with the entire outer surface of said support 10, and then sewn longitudinally, thus creating a tubular element. The stitching (not illustrated in the figure) is performed with reabsorbable or non-reabsorbable suture thread according to the type of material used for the patch.

Once the tubular device or tube has been formed around the support 10, its ends are sutured to the edges 9 of the free ends of the ureter segments by means of head-head stitches 11 (i.e. the two terminal portions of the lumen of the ureter and the tubular device are positioned face to face and sutured by continuous stitch).

It is also possible to use an improved method for connecting the ureter segments and the implant of the present invention, as described in the application MI2012A000646 and in the application U.S. Ser. No. 13/481,135 integrally incorporated here for reference.

Using the above-mentioned procedure, after removal of the urethra/ureter section affected by disease, a small longitudinal incision 4 is made on the outer wall of both the two detached segments 2, 2' in the area of the respective free end which has formed after removal of the necrotic segment 1.

Said incision 4, which forms two edges on each end, is made only on the layer of muscular tissue which forms the outer sheath 5 and 5' (FIG. 2) of the two ureter segments 2, 2', leaving intact the respective underlying urothelial tissue 6 and 6' which maintains its tubular form as far as the free end of said segment 2, 2': in this way the detachment of a portion of outer muscular tissue 5 from the underlying portion of urothelial tissue 6 is obtained.

The length of the edges 4 of muscular tissue created by the incision is such as to leave uncovered a portion of the non-incised underlying urothelial tubular tissue 6 and 6': at this point the ends of the support 10 of the tubular device are fitted over the corresponding free ends of the urothelial tubular tissues 6 and 6' of the segments 2, 2'. Subsequently the edges 4 of the incision will be drawn together and sutured longitudinally with reabsorbable thread thus restoring the tubular outer sheath 5 and 5', suturing the perimeter edge of the support 10 of the tubular device to both said tissues in a sandwich arrangement by means of sutures along the circumference.

In this way it is possible to obtain a homogeneous uniform regrowth of the muscular tissue on the upper surface of the tubular patch and of the urothelial tissue on the lower surface of the support 10.

Without departing from the scope of the invention, a person skilled in the art can make all modifications and improvements to the present invention previously described suggested by normal experience and/or by the natural evolution of the technique.

The invention claimed is:

1. A tubular implant (100) for replacement of one or more ureter(s) and/or urethra segments removed following their resection for the treatment of diseases including necrosis, stenosis, tumors, trauma, iatrogenic injuries, or congenital malformations, the tubular implant (100) consisting of:
   a tubular patch (3) made of a polymeric material; and
   a three-dimensional tubular support (10), positioned inside said tubular patch (3) and not radially expandable, said support (10) being in the form of a mesh provided with openings and made of a moulded and/or thermoformed copolymer of PLA/PGA, or of a moulded and/or thermoformed blend of PLA and PGA, said support (10) having a greater rigidity than a rigidity of the tubular patch (3);

wherein said support (10) is separate from the tubular patch and, in use, is intended to be in contact with an inner surface of said tubular patch, and wherein said tubular patch (3) of the implant (100) is free of any coating of culture cells (cultured tissue cells) previously cultured and/or surface treatment to promote engraftment during regrowth of the autologous tissues and implantable without the coating of culture cells or surface treatment to promote engraftment, wherein the tubular patch (3) has a length shorter than a length of the support (10) so that, in use, the support (10) is not inserted completely inside the one or more ureter(s) and/or urethra segments so as to act as a connecting element between free ends of two detached ureters and/or urethra segments resulting from the one or more ureter(s) and/or urethra segments being removed.

2. The implant according to claim 1, wherein the support (10) has i) a diameter of 10 mm to conform to an adult urethra, or ii) has a diameter of 6 mm with length of 7 mm to conform to a child urethra.

3. The implant according to claim 1, wherein the PGA/PLA of the support (10) is a copolymer of lactic acid and glycolic acid where the PLA is the L-lactic acid (PLLA).

4. The implant according to claim 3, wherein the copolymer PLLA/PGA of the support (10) is formed of 30% PGA and 70% PLLA or is formed of 82-88% in moles of L-lactic acid and 18-12% in moles of glycolic acid.

5. The implant according to claim 1, wherein said tubular patch (3)
i) is made of a PGA fabric or
ii) is a membrane of a polymer used in the medical field
   a) selected from the group consisting of polylactic acid (PLA), polycaprolactone (PCL) or mixtures thereof or
   b) selected from the group consisting of silicone, polysulphone, PE, PP, Polyethylene terephthalate, PTFE, PVC, polypropylene and polystyrene, synthetic Polyamides, Mylar, Polyurethanes, and Polyacrylates.

6. A tubular implant (100) for replacement of one or more ureter(s) and/or urethra segments removed following their resection for the treatment of diseases including necrosis, stenosis, tumors, trauma, iatrogenic injuries, or congenital malformations, the tubular implant (100) consisting of:

a tubular patch (3) made of a polymeric material; and
a three-dimensional tubular support (10), positioned inside said tubular patch (3) and not radially expandable, said support (10) being in the form of a mesh provided with openings and made of a moulded and/or thermoformed copolymer of PLA/PGA, or of a moulded and/or thermoformed blend of PLA and PGA, said support (10) having a greater rigidity than a rigidity of the tubular patch (3), wherein said support (10) is separate from the tubular patch and, in use, is intended to be in contact with an inner surface of said tubular patch, wherein said tubular patch (3) of the implant (100) is free of any coating of culture cells (cultured tissue cells) previously cultured and/or surface treatment to promote engraftment during regrowth of the autologous tissues and implantable without the coating of culture cells or surface treatment to promote engraftment, wherein the tubular patch (3) has a length shorter than a length of the support (10) so that, in use, the support (10) is not inserted completely inside the one or more ureter(s) and/or urethra segments so as to act as a connecting element between free ends of two detached ureters and/or urethra segments resulting from the one or more ureter(s) and/or urethra segments being removed, wherein said tubular patch (3)
i) is made of a PGA fabric or
ii) is a membrane of a polymer used in the medical field
   a) selected from the group consisting of polylactic acid (PLA), polycaprolactone (PCL) or mixtures thereof or
   b) selected from the group consisting of silicone, polysulphone, PE, PP, Polyethylene terephthalate, PTFE, PVC, polypropylene and polystyrene, synthetic Polyamides, Mylar, Polyurethanes, and Polyacrylates, and wherein when said tubular patch (3) is in the form of a polymeric membrane, and incorporates in its thickness a Polyethylene terephthalate reinforcement mesh.

7. An implant (100) ready for use in the replacement of one or more ureter(s) and/or urethra segments removed following their resection for the treatment of diseases including necrosis, stenosis, tumours, trauma, iatrogenic injuries, or congenital malformations, the implant consisting of:

a tubular patch (3) not supported internally and adapted to hold, during regrowth, an autologous tissue which regrows on said tubular patch thus maintaining substantially constant the section of the lumen (8,8') of the section of regrowing ureter and/or urethra, wherein said tubular patch (3) is made of a PGA textured warp knit fabric, wherein said tubular patch (3) is free of any coating of culture cells (cultured tissue cells) previously cultured and/or surface treatment to promote engraftment during regrowth of the autologous tissues so that said tubular patch is ready to be implanted as such without the coating of culture cells to promote engraftment.

8. The implant according to claim 7, wherein said tubular patch (3) is one single piece in tubular form ready for surgical use.

9. The implant according to claim 8, wherein said tubular patch (3) is configured to conform to the urethra and has an internal diameter between 16 and 24 Charrier (where 1 Charrier=1/3 mm) and a thickness of between 0.1 micron and 80 micron.

10. The implant according to claim 2, wherein the PGA/PLA of the support (10) is a copolymer of lactic acid and glycolic acid where the PLA is the L-lactic acid (PLLA).

11. The implant according to claim 10, wherein the copolymer PLLA/PGA of the support (10) is formed of 30% PGA and 70% PLLA or is formed of 82-88% in moles of L-lactic acid and 18-12% in moles of glycolic acid.

12. The implant according to claim 1, wherein the polymeric material is a PGA fabric.

13. The implant according to claim 1, wherein the polymeric material is a PGA warp knit fabric.

14. The implant according to claim 1, wherein the support (10) i) has a diameter of 5 mm with length from 3 to 30 cm to conform to an adult ureter or ii) has a diameter of 3 mm and length from 3 cm to 10 cm to conform to a child ureter.

15. The implant according to claim 8, wherein said tubular patch (3) is configured to conform to the urethra and has an internal diameter between 16 and 24 Charrier (where 1 Charrier=1/3 mm) and a thickness of between 20-30 micron.

16. The implant according to claim 8, wherein said tubular patch (3) is configured to conform to ureters and has an internal diameter between 6 and 10 Charrier (where 1 Charrier=1/3 mm), with a thickness of between 0.1 micron and 80 micron.

17. The implant according to claim 8, wherein said tubular patch (3) is configured to conform to ureters and has an internal diameter between 6 and 10 Charrier (where 1 Charrier=1/3 mm), with a thickness of between 20-30 micron.

18. A tubular implant (100) for replacement of one or more ureter(s) and/or urethra segments removed following their resection for the treatment of diseases including necrosis, stenosis, tumors, trauma, iatrogenic injuries, or congenital malformations, the tubular implant (100) consisting of:
a tubular patch (3) made of a polymeric material; and
a three-dimensional tubular support (10), positioned inside said tubular patch (3) and not radially expandable, said support (10) being in the form of a mesh provided with openings and made of a moulded and/or thermoformed copolymer of PLA/PGA, or of a moulded and/or thermoformed blend of PLA and PGA, said support (10) having a greater rigidity than a rigidity of the tubular patch (3),
wherein said support (10) is separate from the tubular patch and, in use, is intended to be in contact with an inner surface of said tubular patch,
wherein said tubular patch (3) is made of a membrane of a polymer used in the medical field a) selected from the group consisting of polylactic acid (PLA), polycaprolactone (PCL) or mixtures thereof or b) selected from the group consisting of silicone, polysulphone, PE, PP, PET, PTFE, PVC, polypropylene and polystyrene, Nylon (66 or 6), Kevlar and synthetic Polyamides, Mylar, PE, Polyurethanes (Biomer, Pellethane, Corethane and Tecooflex) and Polyureas, Polyacrylates, said membrane being completely coated by a film of turbostratic pyrolytic carbon,
wherein said tubular patch (3) of the implant (100) is free of any coating of culture cells (cultured tissue cells) previously cultured and/or surface treatment to promote engraftment during regrowth of the autologous tissues and implantable without the coating of culture cells or surface treatment to promote engraftment, and
wherein the tubular patch (3) has a length shorter than a length of the support (10) so that, in use, the support (10) is not inserted completely inside the one or more ureter(s) and/or urethra segments so as to act as a connecting element between free ends of two detached ureters and/or urethra segments resulting from the one or more ureter(s) and/or urethra segments being remove.

19. The implant according to claim 7, wherein said tubular patch (3) is shaped in situ in a tubular form from a flat patch during surgery.

* * * * *